(12) United States Patent
Ducker (10) Patent No.: US 10,806,643 B2
(45) Date of Patent: Oct. 20, 2020

(54) ABSORBENT LAMINATE WITH MULTIPLE SUBSTRATES

(71) Applicant: EAM Corporation, Jesup, GA (US)

(72) Inventor: Paul M. Ducker, Brunswick, GA (US)

(73) Assignee: EAM CORPORATION, Jesup, GA (US)

(*) Notice: Subject to any disclaimer, the term of this patent is extended or adjusted under 35 U.S.C. 154(b) by 736 days.

(21) Appl. No.: 15/013,508

(22) Filed: Feb. 2, 2016

(65) Prior Publication Data

US 2016/0220427 A1    Aug. 4, 2016

Related U.S. Application Data

(60) Provisional application No. 62/111,377, filed on Feb. 3, 2015, provisional application No. 62/148,518, filed on Apr. 16, 2015.

(51) Int. Cl.

| A61F 13/539 | (2006.01) |
|---|---|
| A61F 13/534 | (2006.01) |
| A61L 15/60 | (2006.01) |
| A61L 15/58 | (2006.01) |
| D21H 27/34 | (2006.01) |

(Continued)

(52) U.S. Cl.
CPC .......... *A61F 13/539* (2013.01); *A61F 13/534* (2013.01); *A61L 15/58* (2013.01); *A61L 15/60* (2013.01); *D21H 27/32* (2013.01); *D21H 27/34* (2013.01); *D21H 27/38* (2013.01);
(Continued)

(58) Field of Classification Search
CPC .......... A61F 2013/53445; A61F 13/512; A61F 13/51104; A61F 2013/530715; A61F 2013/530737; A61F 13/534; A61F 13/539; A61F 2013/53908; D21H 27/32; D21H 27/34; D21H 27/38
See application file for complete search history.

(56) References Cited

U.S. PATENT DOCUMENTS

| 3,563,243 A * | 2/1971 | Lindquist ................ A61F 13/15 604/369 |
|---|---|---|
| 4,114,621 A | 9/1978 | Mims, Jr. |

(Continued)

FOREIGN PATENT DOCUMENTS

| CN | 1230396 | 10/1999 |
|---|---|---|
| CN | 102781383 | 11/2012 |

(Continued)

OTHER PUBLICATIONS

International Search Report and Written Opinion dated Feb. 2, 2016.
(Continued)

*Primary Examiner* — Peter S Vasat
(74) *Attorney, Agent, or Firm* — Norton Rose Fulbright US LLP (57) ABSTRACT

The present invention relates to an absorbent laminate structure, and disposable absorbent article incorporating the structure, wherein first and second absorbent matrices comprising particulate superabsorbent polymeric material and filamentary adhesive are arranged between two outer substrate layers. The relatively porous, intermediate or central substrate layer, positioned between the absorbent matrices, promotes liquid transport within the laminate structure.

13 Claims, 3 Drawing Sheets

(51) Int. Cl.
  *D21H 27/32* (2006.01)
  *D21H 27/38* (2006.01)
(52) U.S. Cl.
  CPC .............. *A61F 2013/53445* (2013.01); *A61F 2013/53908* (2013.01)

(56) References Cited

U.S. PATENT DOCUMENTS

| | | | |
|---|---|---|---|
| 4,573,986 | A | 3/1986 | Minetola et al. |
| 4,670,011 | A | 6/1987 | Mesek |
| 4,940,464 | A | 7/1990 | Van Gompel et al. |
| 5,458,592 | A | 10/1995 | Abuto et al. |
| 5,486,167 | A | 1/1996 | Dragoo et al. |
| 5,494,622 | A * | 2/1996 | Heath .............. A61F 13/15658 156/276 |
| 5,520,673 | A | 5/1996 | Yarbrough et al. |
| 5,552,012 | A * | 9/1996 | Morris .............. A61F 13/15658 156/272.4 |
| 5,558,655 | A | 9/1996 | Jezzi et al. |
| 5,562,645 | A * | 10/1996 | Tanzer .............. A61F 13/15203 604/358 |
| 5,593,399 | A | 1/1997 | Tanzer et al. |
| 5,785,696 | A | 7/1998 | Inoue et al. |
| 5,944,706 | A | 8/1999 | Palumbo et al. |
| 6,037,518 | A | 3/2000 | Guidotti et al. |
| 6,191,340 | B1 | 2/2001 | Carlucci et al. |
| 6,316,687 | B1 | 11/2001 | Davis et al. |
| 6,372,953 | B1 | 4/2002 | Young et al. |
| 6,380,456 | B1 | 4/2002 | Goldman |
| 6,436,234 | B1 | 8/2002 | Chen et al. |
| 6,455,114 | B1 | 9/2002 | Goldhirsch et al. |
| 6,479,415 | B1 | 11/2002 | Erspamer et al. |
| 6,610,903 | B1 | 8/2003 | Latimer et al. |
| 6,646,180 | B1 | 11/2003 | Chmielewski |
| 6,667,424 | B1 | 12/2003 | Hamilton et al. |
| 6,746,976 | B1 | 6/2004 | Urankar et al. |
| 6,923,926 | B2 | 8/2005 | Walter et al. |
| 6,976,978 | B2 | 12/2005 | Ruman et al. |
| 7,910,797 | B2 | 3/2011 | Nandrea et al. |
| 8,039,684 | B2 | 10/2011 | Guidotti et al. |
| 9,238,089 | B2 | 1/2016 | Chmielewski et al. |
| 9,398,986 | B2 | 7/2016 | Pasqualoni et al. |
| 10,092,674 | B2 | 10/2018 | Chmielewski et al. |
| 2003/0018311 | A1 | 1/2003 | Graef et al. |
| 2003/0135178 | A1* | 7/2003 | Hansen .................. A61F 13/535 604/368 |
| 2003/0225384 | A1 | 12/2003 | Zenker et al. |
| 2004/0054343 | A1 | 3/2004 | Barnett et al. |
| 2005/0118916 | A1* | 6/2005 | Ducker .............. A61F 13/15203 442/385 |
| 2010/0256584 | A1 | 10/2010 | Litvay |
| 2010/0318047 | A1 | 12/2010 | Ducker et al. |
| 2011/0162989 | A1* | 7/2011 | Ducker .............. A61F 13/5323 206/389 |
| 2011/0208145 | A1 | 8/2011 | Zhang et al. |
| 2012/0004632 | A1 | 1/2012 | Zhang et al. |
| 2012/0053545 | A1 | 3/2012 | Love et al. |
| 2012/0144790 | A1 | 6/2012 | Cambo et al. |
| 2013/0046263 | A1 | 2/2013 | Fukudome et al. |
| 2014/0276510 | A1 | 9/2014 | Ducker et al. |
| 2014/0315034 | A1 | 10/2014 | Akiyama et al. |
| 2015/0245958 | A1 | 9/2015 | Chmielewski et al. |
| 2016/0220427 | A1 | 8/2016 | Ducker |
| 2017/0065466 | A1 | 3/2017 | Szypka |
| 2017/0258651 | A1 | 9/2017 | Hammons et al. |
| 2019/0328587 | A1 | 10/2019 | Saevecke et al. |

FOREIGN PATENT DOCUMENTS

| | | |
|---|---|---|
| CN | 102970953 | 3/2013 |
| EP | 0556996 | 8/1993 |
| JP | 2003026701 | 1/2003 |
| JP | 2005537852 | 12/2005 |
| WO | WO1995/013776 | 5/1995 |
| WO | WO 1996/005790 | 2/1996 |
| WO | WO1999/049826 | 10/1999 |
| WO | WO2000/038749 | 7/2000 |
| WO | WO2000/075427 | 12/2000 |
| WO | WO2004/012639 | 2/2004 |
| WO | WO 2014/144131 | 9/2014 |

OTHER PUBLICATIONS

Extended European Search Report Issued in Corresponding European Application No. 16747100.2, dated Jun. 4, 2018.
Ducker, Paul M ; Issue Notification for U.S. Appl. No. 14/212,754, filed Mar. 14, 2014, dated Dec. 29, 2015, 1 pg.
Ducker, Paul M.; Corrected Notice of Allowability for U.S. Appl. No. 14/212,754, filed Mar. 14, 2014, dated Sep. 25, 2015, 8 pgs.
Ducker, Paul M.; Non-Final Office Action for U.S. Appl. No. 14/212,754, filed Mar. 14, 2014, dated Jan. 14, 2015, 21 pgs.
Ducker, Paul M.; Notice of Allowance for U.S. Appl. No. 14/212,754, filed Mar. 14, 2014, dated Aug. 17, 2015, 9 pgs.
Ducker, Paul M.; U.S. Patent Application entitled: Absorbent Structure With Discrete Acquisition Cells, having U.S. Appl. No. 14/212,754, filed Mar. 14, 2014, 30 pgs.
International Preliminary Report for corresponding Application No. PCT/US2014/028292, dated Sep. 15, 2015.
International Preliminary Report for corresponding Application No. PCT/US2014/028414, dated Sep. 15, 2015.
International Search Report and Written Opinion for corresponding Application No. PCT/US2014/028292, dated Aug. 11, 2014.
International Search Report and Written Opinion for corresponding Application No. PCT/US2014/028414, dated Mar. 14, 2014.
International Search Report and Written opinion issued in International Application No. PCT/US2019/034201, dated Sep. 9, 2019.
Office Action issued in Chinese Patent Application No. 201480021203.7, dated Mar. 2, 2018.
Office Action issued in counterpart Chinese Application No. 201680011883.3, dated Mar. 3, 2020. (English Translation Provided).
Office Action issued in Japanese Patent Application No. 2016-502781, dated Mar. 26, 2018.

* cited by examiner

ABSORBENT LAMINATE WITH MULTIPLE SUBSTRATES

CROSS-REFERENCE TO RELATED APPLICATIONS

This is a non-provisional application claiming priority to U.S. Provisional Ser. No. 62/111,377, filed on Feb. 3, 2015 and U.S. Provisional Ser. No. 62/148,518, filed on Apr. 16, 2015, both entitled "Absorbent Laminate With Multiple Substrates", both of which are hereby incorporated by reference in their entirety.

TECHNICAL FIELD

The present invention relates generally to an absorbent laminate suited for use in disposable absorbent products, and more particularly to a layered absorbent laminate comprising absorbent matrices of particulate superabsorbent polymer and filamentary adhesive, with a central substrate exhibiting relatively high porosity to promote liquid distribution within the laminate.

BACKGROUND OF THE INVENTION

Disposable absorbent articles such as sanitary napkins, diapers, pantiliners, and adult incontinence products have become thinner and more garment-like. To produce thin, flexible absorbent structures with the necessary static and dynamic absorbent characteristics for these products, manufacturers have increasingly turned to the use of fluid storage cores containing superabsorbent polymers (SAP), a technology well known to those skilled in the art, to provide the necessary absorbent capacity in a compact structure. Since thin absorbent cores are generally low in void volume, in many applications they do not absorb liquid as rapidly as it is presented to the product. Various low-density acquisition layers, well known to those skilled in the art, are frequently placed on top of these storage cores to provide the function of capturing gushes of bodily fluids, controlling the fluid, and then metering it into the adjacent storage core.

One of the important interactions between the storage core and the acquisition layer is that between liquid insults, the storage core ideally extracts fluid out of the acquisition layer, which in concert with the typical coverstock, presents a more dry surface to the skin of the wearer, a product attribute generally considered important. Additionally, it returns the acquisition layer more towards its dry state, making it more able to manage the next gush of bodily fluid.

The use of absorbent laminates in which SAP is sandwiched between light weight substrates, has made it possible to provide storage cores with a high percentage of SAP while being very thin, flexible, and drapeable. One of the absorbent laminate technologies utilizes hot melt adhesive fibers to stabilize the particulate SAP and bond the laminate, and this technology is effective at providing materials with good flexibility and wet integrity.

One shortcoming of absorbent laminates such as this, however, is that it has been observed that despite the high SAP content and SAP percentage by weight made possible by this technology, these laminates do not dry the adjacent acquisition layer as well as would be desirable for materials with such a high SAP content.

What is needed is a laminate that better utilizes the SAP to dry the adjacent acquisition layer or product surface while generally preserving the thinness, flexibility, drapeability, tensile strength, and cost effectiveness of the laminate.

SUMMARY OF THE PRESENT INVENTION

In accordance with the present invention, a disposable absorbent laminate comprises at least three substrate layers, and at least first and second absorbent matrices respectively positioned between adjacent ones of the substrate layers. Each of the three substrate layers, including first and second outer layers, and a third intermediate substrate layer, comprises cellulosic fibrous material, and they each preferably comprise tissue. Each of the absorbent matrices comprises particulate superabsorbent polymeric (SAP) material, and a network of filamentary adhesive, with the filamentary adhesive adhering to and stabilizing the particulate superabsorbent polymeric material, and adhering adjacent ones of the substrate layers to each other to resist delamination of the absorbent laminate.

Notably, in accordance with the present invention, the third, intermediate one of the substrate layers is specifically selected to exhibit a high Frazier Porosity and a relatively greater Frazier Porosity than the first and second, outer substrate layers. Development of the present invention has shown by providing a high porosity value in the intermediate substrate layer and a differential porosity within the laminate structure, the drying effect of the material of the present invention on adjacent materials is improved, thereby promoting the efficient use of the particulate superabsorbent material. It is believed that the resulting structure in some manner more effectively transmits the absorbent suction generated by the SAP particulate to the surface of the laminate by way of capillary action to extract fluid absorbed in adjacent layers. It is also believed that by providing a highly porous intermediate substrate, the laminate structure becomes somewhat "hollow" with this porous layer functioning in an analogous manner to the internal gap between two layers of a two-ply paper towel to rapidly capture and spread liquid. This is believed to be particularly helpful when the liquid is somewhat viscous, such as in feminine hygiene applications. It is thought that spreading fluid over a larger area of core results in lower levels of core saturation, again enhancing the ability to extract liquid from adjacent layers. This is achieved while maintaining the tensile strength imparted to the material by the first and second outer substrate layers, which tend to be stronger than the highly porous intermediate substrate.

It is presently contemplated that each of the first, second, and third substrate layers comprise tissue, but it is within the purview of the present invention that other cellulosic material can be employed. In particular, the relatively porous, third, intermediate substrate layer may comprise spunlace nonwoven comprised of cellulosic fiber, in order to create a highly porous substrate layer. Alternatively, the relatively porous intermediate substrate may comprise creped tissue, which is elongated, removing the crepe, to provide the desired porosity.

In the preferred form, the third, intermediate one of the substrate layers exhibits a Frazier porosity of at least about 300 $feet^3/minute/foot^2$.

It is contemplated that the third, intermediate substrate layer exhibits a Frazier porosity that is greater than the Frazier porosity of the first and second outer substrate layers by at least about 70 $feet^3/minute/foot^2$, more preferably by at least about 100 $feet^3/minute/foot^2$, and more preferably by about 150 $feet^3/minute/foot^2$. The less porous outer substrate layers tend to be higher in tensile strength, and as a result, this structure leaves two of these stronger layers in place, maintaining the tensile strength of the laminate at a similar level as a laminate comprising the outer layers without the highly porous intermediate substrate layer, which tends to be relatively weak in tensile.

By configuring the present laminate layers to exhibit the above-described absolute and differential porosity, the function of efficient extraction of fluid from adjacent layers by the laminate is promoted, while the structure still exhibits desired flexibility and tensile strength which are properties that make these laminates attractive as storage core materials. In the preferred form, the absorbent laminate exhibits a modified circular bend value of less than about 30 gramsF, with the laminate exhibiting a tensile strength of at least about 10 Newtons per 50 mm (N/50 mm).

The absorbent laminate of the present invention may be readily configured as a disposable absorbent article, by positioning the absorbent laminate in operative association with a liquid permeable topsheet, positioned above the absorbent laminate, with an acquisition/distribution layer positioned between the topsheet and the absorbent laminate. A disposable article employing the absorbent laminate may further include a liquid impermeable back sheet positioned beneath the absorbent laminate, which is typically employed for providing the disposable absorbent article with the desired containment characteristic.

Other features and advantages of the present invention will become readily apparent from the following detailed description, the accompanying drawings, and the appended claims.

DETAILED DESCRIPTION OF THE INVENTION

While the present invention is susceptible of embodiment in various forms, there are shown in the drawings, and will hereinafter be described, presently preferred embodiments of the invention, with the understanding that the present disclosure is to be considered as an exemplification of the invention, and is not intended to limit the invention to the specific embodiments disclosed herein.

The present invention generally relates to laminated materials containing particulate superabsorbent polymeric (SAP) materials, and associated substrates which are integrated with the particulate SAP by filamentary adhesive networks to provide an integrated laminate structure exhibiting desired absorbent properties, as well as desired flexibility and tensile strength.

In accordance with the present invention, an absorbent laminate comprises first, second, and third substrates, which each may advantageously comprise tissue, and first and second absorbent matrices, each comprising the particulate SAP material, which is stabilized and integrated with the substrates by the filamentary adhesive networks.

Notably, the present invention contemplates that the laminate structure exhibit a high Frazier Porosity in an intermediate central substrate, and a differential porosity, in that the porosity an intermediate, central one of the substrates is significantly greater than the porosity of a pair of outer ones of the substrates. The resultant structure can be configured to exhibit requisite tensile strength to permit use of the laminate in converting operations for manufacture of disposable absorbent articles, with the relatively porous intermediate substrate acting in the nature of a somewhat "hollow" region promoting desired capillary effects and liquid transport and distribution within the laminate structure.

In illustrated embodiments, first, second, and third substrates are provided, with first and second absorbent matrices, each comprising particulate SAP and filamentary adhesive, respectively positioned between adjacent ones of the substrates. In accordance with the present invention, a third, intermediate one of the substrate is selected to exhibit relatively high porosity, thus providing the laminate structure with a "hollow", relatively porous central region, which is observed to promote liquid transport and spreading within the laminate. The addition of the highly porous intermediate substrate is observed to promote the extraction of liquid from adjacent materials by the laminate, even though it might be supposed that a more dense cellulosic tissue with smaller pores would be able to transmit a higher level of capillary suction to adjacent layers. This supposition was not supported by the lab data.

An absorbent laminate formed in accordance with the present invention is suited for use in converting operations as a raw material in the form of continuous running packages such as rolls or festooned bales. In the case of festooned bales, particularly when the slit width is narrow, it is very difficult to guarantee that one particular side of the material remain oriented to the top of the product while it is being converted as a raw material component into absorbent articles. There is significant value in having a material that is symmetrical, in a Z-direction, with respect to either side facing upwards, so that the material can twist and flip over with no consequence. By having the highly porous substrate layer in the center, the laminate of the present invention can be symmetrical with respect to flipping over. The present absorbent laminate is suitable for use in disposable absorbent articles such as sanitary napkins, pantiliners, absorbent products for incontinence, and other disposable absorbent articles worn close to a wearer's body. Although the invention will be described herein with reference to a sanitary napkin 10, the invention may be utilized with other disposable sanitary absorbent articles or any other converted article that includes a laminated material that contains particulate, supplied to the converting operation in continuous running pre-packaged form.

Figure 1:
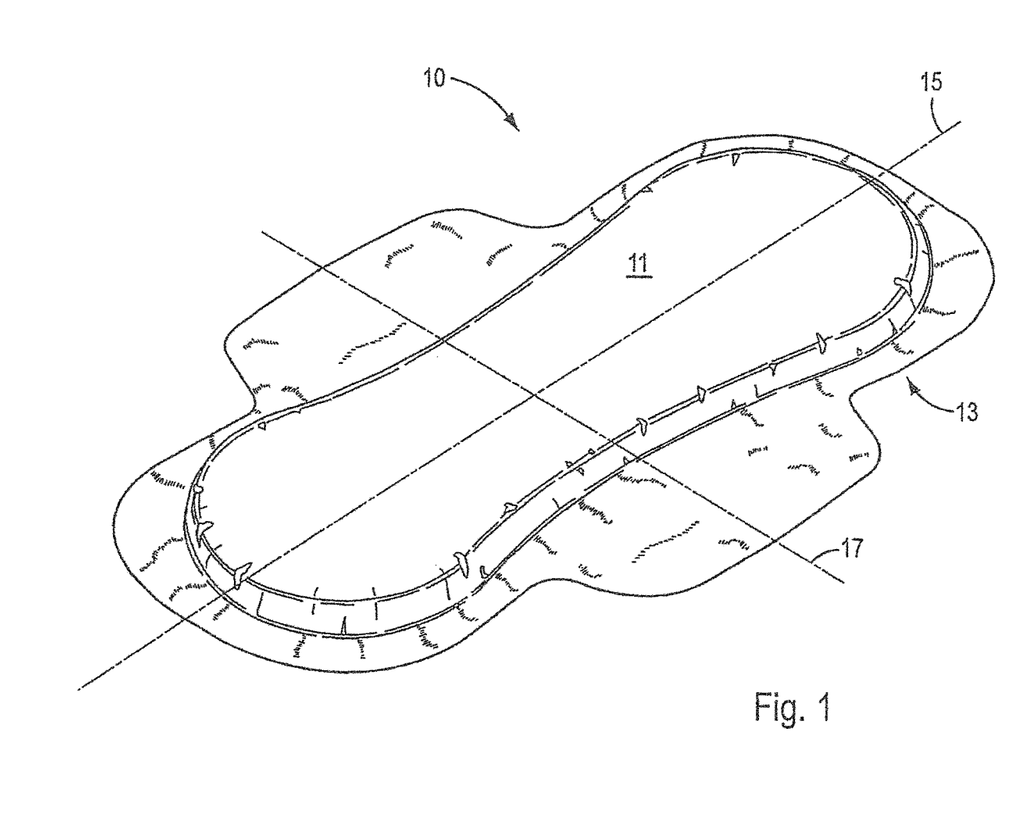
FIG. 1 is a perspective view of a disposable absorbent article including a multiple substrate absorbent laminate according to the present invention.

As shown in FIG. 1, a disposable absorbent article incorporating the absorbent laminate of the present invention is illustrated as a sanitary napkin 10 for absorbing bodily fluids. The sanitary napkin 10 includes a body facing surface 11, a garment facing surface 13, a longitudinally extending centerline 15, and a transversely extending centerline 17.

Figure 2:
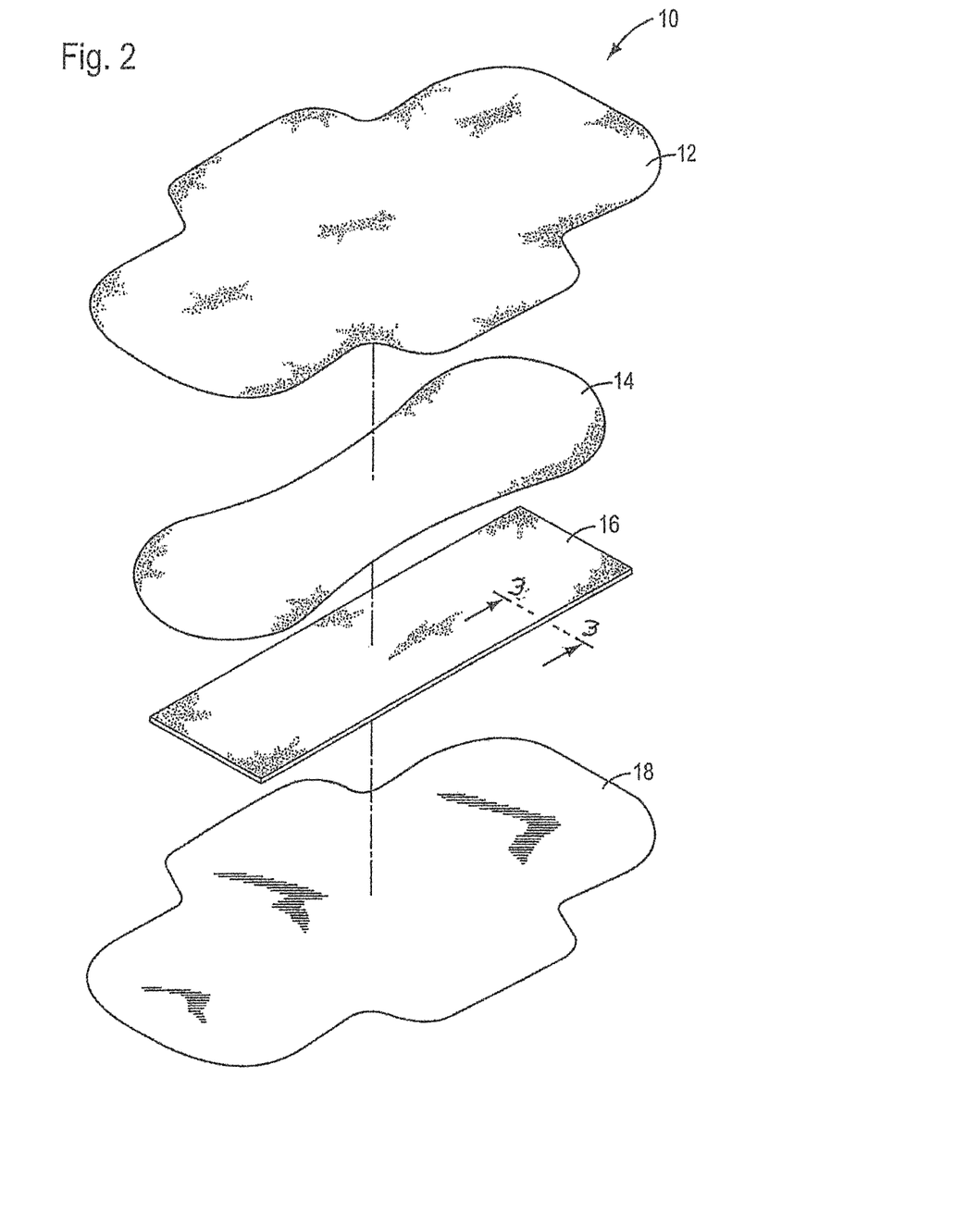
FIG. 2 is an exploded view of the absorbent article shown in FIG. 1.

As best seen in the exploded view shown in FIG. 2, the sanitary napkin 10 includes, a liquid permeable topsheet or cover layer 12, a multiple substrate absorbent laminate structure 16 embodying the present invention, an acquisition/distribution or transfer layer 14 arranged between the cover layer 12 and the absorbent laminate structure 16, and a liquid impermeable backsheet or barrier layer 18.

As known to those skilled in the art, the cover layer 12 may comprise a relatively low density, bulky, high-loft non-woven web material, and may be composed of only one type of fiber, such as polyester or polypropylene or it may include a mixture of more than one fiber. The cover may be composed of bi-component or conjugate fibers having a low melting point component and a high melting point component. The cover layer 12 preferably has a necessary degree of wettability, although the individual fibers comprising the cover may not be particularly hydrophilic. The cover material should also contain a great number of relatively large pores. This is because the cover layer 12 is intended to take-up body fluid rapidly and transport it away from the body and the point of deposition.

Alternatively, as known in the art, the cover layer 12 can also be made of polymer film having large pores. Because of such high porosity, the film accomplishes the function of quickly transferring body fluid to the inner layers of the absorbent system.

Adjacent to the cover layer 12 on its inner side and bonded to the cover layer 12 is an optional acquisition/distribution or transfer layer 14. The transfer layer 14 provides the means of receiving body fluid from the cover layer 12 and holding it until the underlying absorbent laminate structure 16 has an opportunity to absorb the fluid. The transfer layer 14 preferably contains large pores with large voids that enables the layer to quickly absorb large quantities of liquid and hold it away from the outer side of the cover layer 12, thereby preventing the liquid from re-wetting the cover layer 12 and its surface. In this way the transfer layer 14 functions to quickly absorb liquid and then transmit the liquid to the underlying absorbent laminate structure 16. The optional transfer layer 14 may be composed of fibrous materials, such as wood pulp, polyester, rayon, flexible foam, or the like, or combinations thereof. The transfer layer 14 may also comprise thermoplastic fibers for the purpose of stabilizing the layer and maintaining its structural integrity.

Figure 3:
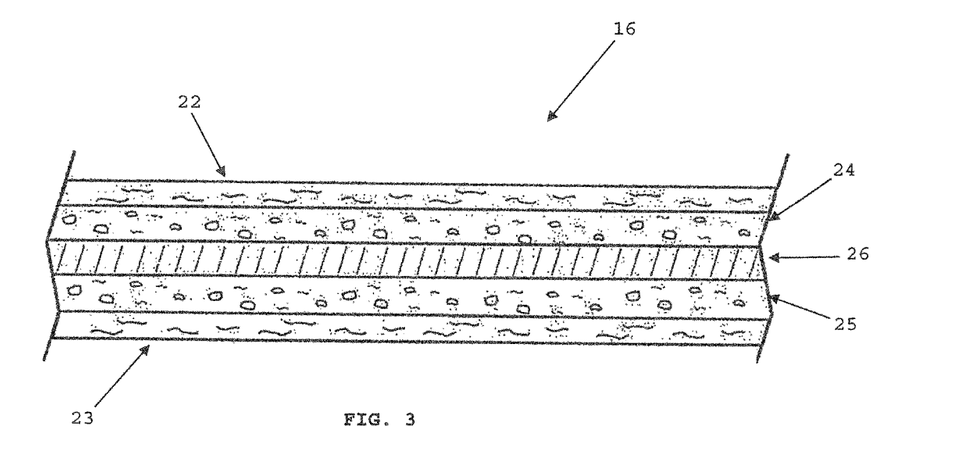
FIG. 3 is a cross-sectional view taken along lines 3-3 of FIG. 2 showing the absorbent laminate of the present invention.
Figure 4:
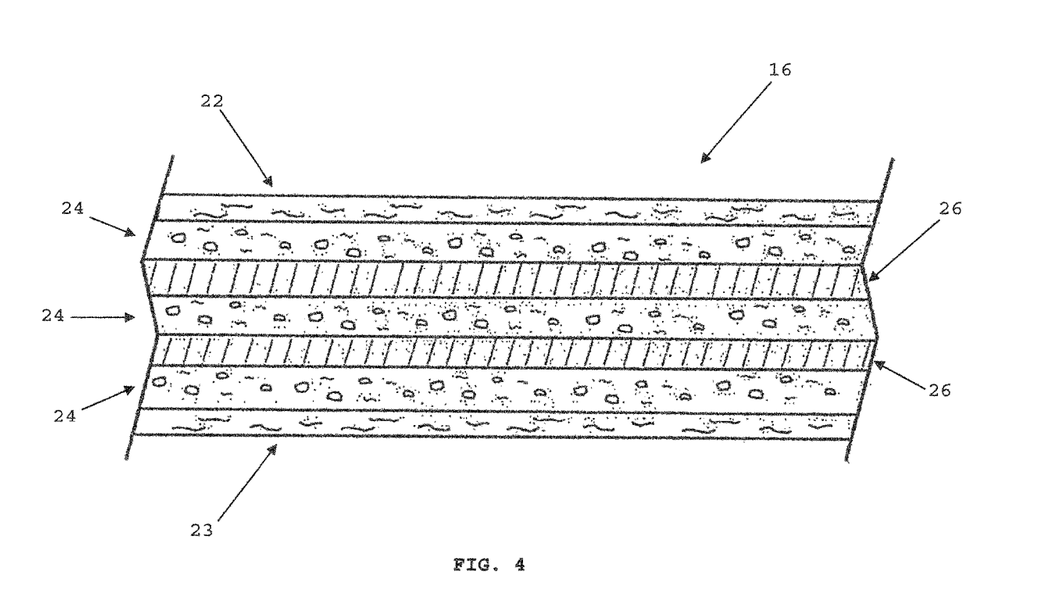
FIG. 4 is a cross-sectional view similar to FIG. 3 showing an alternative embodiment of the absorbent laminate of the present invention.

As best seen in FIGS. 3-4, the multiple substrate, absorbent laminate structure 16 according to the present invention is a multi-layer core construction including a first, second, and third substrate layers, and first and second absorbent matrices, each comprising particulate superabsorbent polymeric (SAP) material, and filamentary adhesive. The absorbent matrices are respectively positioned between adjacent ones of the substrate layers to provide the desired laminate structure. Notably, in accordance with the present invention, the laminate construction is configured to exhibit differential porosity, in that a central, intermediate one of the substrate is selected to exhibit a relatively high porosity, which desirably promotes liquid transport within the laminate structure.

As stated above, the laminate of the present invention is comprised of a first tissue facing layer, a first absorbent matrix in the form of a layer of SAP particles mixed with hot melt adhesive fibers, one or more highly porous center layers, optionally separated by additional layers of SAP particles mixed with hot melt adhesive fibers, a second absorbent matrix comprising particulate SAP and filamentary adhesive, and finally a second tissue facing layer. High porosity in the intermediate layer and differential porosity for the structure is achieved by selecting the central or intermediate substrate layer to have a high Frazier Porosity and exhibit greater porosity than the first and second outer substrate layers, which may be selected to exhibit the same porosity, while providing the laminate with the desired tensile strength.

The present invention provides an absorbent laminate with improved drying properties comprised of SAP laminated between substrates and held in-place with hot melt adhesive fibers. The laminate of the present invention is comprised of the following layers: a first substrate in the form of tissue facing layer or substrate (22, in FIG. 3), and an absorbent matrix comprising a layer of SAP particles mixed with filamentary, hot melt adhesive fibers to form a first absorbent matrix (24 in FIG. 3), optionally in a discontinuous monolayer of particles. The laminate further includes a highly porous center substrate layer of tissue or cellulosic spunlace (26 in FIG. 3), with a Frazier Porosity preferably of at least about 300 cubic feet per minute per square foot ($foot^3$/minute/$foot^2$), and more preferably exceeding 320 cubic foot per minute per square foot, a second absorbent matrix comprising a layer of SAP particles mixed with filamentary hot melt adhesive fibers (25 in FIG), optionally in a discontinuous monolayer of particles, and a second substrate in the form of tissue facing layer (23 in FIG. 3). The central, intermediate highly porous layer 26 thus comprises the third substrate of the laminate absorbent structure. In other embodiments, there can be multiple highly porous center layers of tissue separated by additional layers of a mixture of SAP and adhesive fibers.

The laminate material of the present invention is thin, with a caliper of 1.5 millimeters or less, and drapeable, with a modified circular bend (MCB) value less than 30 gF. The material is also highly absorbent with a SAP percentage in the range of 15%-80%, and has tensile strength greater than 10 Newtons per 50 mm (N/50 mm).

Counterintuitively, the laminate of the present invention provides a better drying effect compared to prior art laminate that has a higher amount and percentage of the same SAP and yields higher free swell absorbency and centrifuge retention.

First and Second Facing Layers:

The first and second facing layers (22, 23, FIG. 3) are tissue, and are less porous than the highly porous center substrate layer. This serves to contrast with the highly porous center layer to create the desired "hollow" sheet. Frazier Porosity is in the range of 30 cu ft/min./sq ft to 300 cu ft/min/sq ft, and more ideally in the range of 150-250 cu ft/min/sq ft. The basis weight is in the range of 10-30 gsm, and more ideally in the range of 15-20 gsm. Examples of suitable facing layers would be 17 gsm 3995 tissue from Dunn Paper or 16.3 gsm 3207 tissue, also from Dunn Paper. These materials are light enough to impart flexibility in the laminate and are strong enough in tensile to provide the necessary tensile strength.

Highly Porous Center Layer:

The highly porous center layer of the present invention, which provides the third substrate layer (26 in FIG. 3) is comprised of a tissue with a very high Frazier Porosity. The Frazier Porosity of the center tissue ideally has a Frazier Porosity of at least 320 cu ft/min/sq ft. It more ideally has a Frazier Porosity exceeding 350 cu ft/min/sq ft. While not wanting to be bound by any particular theory, it is believed that having a highly porous center layer with a Frazier porosity higher than the facing layers creates a "hollow" sheet, which it is believed enhances the spreading of the fluid within the sheet, thereby involving more of the SAP and improving the drying power. In the case of a highly porous center layer comprised of tissue, the basis weight is in the range of 10 gsm to 30 gsm, and more ideally 15 gsm to 25 gsm. One example of a suitable highly porous tissue is 17 gsm 3008 tissue from Dunn Paper. Another suitable example of an even more highly porous tissue is 1113 creped wadding, also commercially available from Dunn Paper, with the crepe pulled out by elongating the tissue in the machine direction, bringing the resulting basis weight down to around 17 gsm. The highly porous center layer can also be a spunlace material comprised of cellulosic fibers, which can be natural, such as cotton, or regenerated, such as Viscose or Tencel. In the case of a highly porous center layer comprised of spunlace nonwoven, the basis weight is ideally in the range of 20-35 gsm, more ideally in the range of 20-30 gsm. Spunlace in this basis weight range would be expected to have Frazier Porosity even higher than that of highly porous tissue of similar basis weight.

Superabsorbent Polymer (SAP):

The SAP utilized in the present invention is advantageously any SAP type that is suitable for use in the manufacture of disposable absorbent articles such as sanitary napkins, pantiliners, adult incontinence products, diapers and the like. This is a developed technology and selecting a superabsorbent polymer from the choice of commercially available SAP types is well known to those skilled in the art. The type of SAP most advantageously used in the laminate of the present invention is dependent on the type of product the product is going to be used in. A feminine hygiene application may use SA60n commercially available from Sumitomo Seika in Singapore, which has a high centrifuge retention. A urine application may more suitably use a SAP that is more highly crosslinked and has a higher gel strength such as T9030 commercially available from BASF.

The SAP particle size distribution for the laminate of the present invention should fall within the range typical of SAP commercially used in disposable hygiene products.

In the laminate of the present invention, at least one of the SAP layers should advantageously be of a basis weight where most of the SAP particles are one layer thick in particles or less. Given the general particle size distribution for most commercially available SAP grades that are used commercially in producing disposable absorbent articles, this has been observed to be around 100 gsm or less. More desirably, the SAP layers are in the range of 40 gsm to 10 gsm, and even more desirably, are in the range of 30 gsm to 15 gsm. In material grades where it is desirable to have higher SAP content in order to meet absorbency requirements for a particular application, it is preferable to add additional alternating layers of SAP/filamentary adhesive (24 in FIG. 4,) and highly porous middle layers (26 in FIG. 4), or alternatively building a core out of several layers of the laminate material of the present invention. Less desirable, but still within the scope of the present invention, is to have at least one SAP layer less than 100 gsm and the other SAP layer higher than that.

Hot Melt Adhesive:

The SAP of the present invention is mixed with hot melt adhesive fibers of the type produced by commercially available meltblown-type glue heads widely used in the manufacture of disposable absorbent articles and well known to those skilled in the art. The hot melt adhesive can be any pressure sensitive adhesive suitable for use in the high speed manufacture of disposable absorbent articles, with the necessary rheology to form glue fibers in the commercially available meltblown systems. A most suitable hot melt adhesive is a tacky pressure sensitive synthetic rubber based adhesive, including the Styrene-Butadiene-Styrene (SBS) or Styrene-Isoprene-Styrene (SIS) block copolymer based adhesive types.

The hot melt is most advantageously added in quantities necessary to produce materials that have lamination strengths strong enough to sustain the mechanical forces applied during converting, but not excessive amounts that would interfere with the SAP swelling. The amount of adhesive required varies according to adhesion and cohesion properties of the adhesive type but adhesive quantities in the range of 2%-10% of the add-on weight of the SAP would not be atypical. A suitable adhesive is NW1023AAZP commercially available from HB Fuller.

The laminate of the present invention is thin, with a caliper of 1.5 millimeters or less, and drapeable, with a modified circular bend (MCB) value less than 30 gF. The material is also highly absorbent with a SAP percentage in the range of 15%-80%, and has tensile strength greater than 10 N/50 mm.

The laminate of the present invention is desirably formed as a continuous web by unrolling a moving web of the first facing tissue, metering a continuous curtain of the first SAP layer and mixing hot melt adhesive fibers ejected from a commercially available meltblown type hot melt applicator well known to those skilled in the art, which adheres the SAP to the first facing tissue. Then the highly porous middle layer is unrolled and provided as a moving web and laminated to the tacky first SAP and hot melt adhesive fiber layer. Then a second layer of SAP and hot melt adhesive fibers is added to the highly porous middle layer, in the same manner as the first SAP and hot melt fiber layer. Finally a moving web comprised of the second facing tissue is unrolled and laminated to the tacky second SAP and hot melt adhesive fiber layer.

Absorbent matrices comprising superabsorbent polymeric material and filamentary adhesive can be formed in accordance with the teachings of US Patent Publication No. 2011/0162989, published Jul. 7, 2011, the disclosure of which is hereby incorporated by reference.

Example 1

A laminate of the present invention was made as described above using 17 gsm 3995 tissue from Dunn Paper as the facing layers, and 17 gsm 3008 tissue from Dunn Paper as the highly porous middle layer. The first and second layers of SAP disposed between the highly porous center tissue and the first or second facing tissue layers each contained roughly 35 gsm of SA65s from Sumitomo Seika and each layer was mixed with approximately 2 gsm E60W hot melt adhesive fibers from Savare, ejected by an ITW Dynatec UFD Dynafiber glue applicator head. The resulting material had a basis weight target of 125 gsm, and a SAP content target of around 70 gsm. The highly porous tissue layer material has a Frazier Porosity of around 350 cu ft/min/sq ft. The facing layers have a Frazier Porosity of around 210 cu ft/min/sq ft. A trial sample of the material of Example 1 had an average tensile strength of 15 N/50 mm and an average caliper of 0.97 mm.

Example 2

A laminate of the present invention was made as described in Example 1 above using similar materials and steps, except the SAP content was around 38 gsm in each SAP layer, and the highly porous middle layer was made from 1113 Creped Wadding commercially available from Dunn Paper, and elongated under tension in the machine direction pulling the crepe out of the tissue thus opening the holes in the sheet until it had a basis weight of around 17 gsm. While Frazier porosity data is not available for this elongated creped wadding, a piece of 3008 tissue of the type used in Example 1 above was supported by 18 mesh window screen placed over the hose end of a shop vacuum and the available vacuum drawn through the sample produced a 4.7-inch H2O pressure drop read on a Magnahelic gauge. The 3008 tissue sample was replaced by a sample of 1113 tissue, elongated as described in example 2 and this yielded a pressure drop of 2.0 inches H2O, suggesting the elongated 1113 tissue is more porous to air flow than the 3008 tissue. A trial sample of the material of example 2 had an average tensile strength of 15.1 N/50 mm and an average caliper measurement of 0.88 mm.

Control 1:

A laminate of the prior art was made as described above using 16.3 gsm 3207 tissue from Dunn Paper as the facing layers. No highly porous middle layer was used and only a single layer of a mixture of SAP and hot melt adhesive fibers was laminated between the facing layers. The mixture was comprised of around 81.4 gsm of SA65s SAP from Sumitomo and around 6 gsm of NW1023AAZP hot melt adhesive from HB Fuller for an overall basis weight target of 120 gsm. The 3207 tissue has a Frazier Porosity of around 60 cu ft/min/sq ft. Control 1 has a higher SAP content than either example 1 or example 2 above. Samples of control 1 had an average tensile strength of 24.8 N/50 mm and an average caliper of 0.92 mm.

Control 2:

A laminate was made as described above using 3 layers of 16.3 gsm 3207 tissue as the facing and center layers separated by layers of SAP mixed with not melt adhesive fibers. Each SAP layer had around 32.5 gsm SAP, and around 3 gsm Savare E60W adhesive. The relatively low Frazier porosity of the 3207 tissue causes this control not to have a highly porous center layer and not to be a "hollow" sheet.

Control 1+Tissue:

The laminate of Control 1 was placed on top of a layer of 17 gsm 3008 tissue from Dunn Paper. Rather than have the 3008 tissue arranged in the structure as a highly porous middle layer, it is instead added underneath and was unbonded.

Control 3:

This was J1800930 grade NovaThin® Hydrogen bonded airlaid core, commercially available from EAM Corporation in Jesup, Ga. This is a hydrogen bonded airlaid material comprised of a mixture of cellulose fibers and SAP, 1.80 gsm in basis weight containing 51 gsm SA65s from Sumitomo. Rather than being a laminate such as the other examples, this is a mixture of SAP pulp fibers that have been airlaid using conventional airlaid equipment and hydrogen bonded. This control is include to illustrate the greater drying efficiency of the pulp/SAP matrix but also illustrate how much stiffer this type of material is compared to the laminates of the present invention.

Tensile Test:

This test references Edana Method "Tensile Strength" 20.2-89. A 240 mm×50 mm sample is cut, with the long dimension oriented in the machine direction, and placed in tensile tester jaws spaced 200 mm apart. After snugging the sample to a 2 N pre-tension, the tensile tester jaws move apart at 100 mm per minute until the sample breaks. The maximum force is recorded in Newtons and is reported as Tensile in units of Newtons per 50 mm.

Test Fluid:

A viscous test fluid was prepared as follows: 500 ml of prepared 0.9% saline (prepared by Lab Chem) was weighed in a glass beaker and then 10.0 g of Sodium Carboxymethylcellulose powder (from Hercules) was added. The mixture was heated and stirred until the Sodium CMC was fully dissolved. After cooling to room temperature, the viscosity of the mixture measured at about 21 centipoise using a Brookfield viscometer.

Acquisition and Fluid Retention in an Acquisition Layer:

200 mm×300 mm hand sheet samples of each of the example and control materials were weighed and the basis weight recorded and then were arranged flat on the bench top. A representative high-loft resin bonded acquisition layer with a measured basis weight of around 47 gsm and a designation of grade 68728 from PGI was cut into pieces 65 mm×250 mm and the dry weight of each piece was recorded. The resin bond acquisition layer pieces were placed on the example materials and the center marked with a pen marking both the core and the acquisition layer. A strike plate made out of ½ inch lexan, 65 mm×250 mm with a 1-inch round hole in the center, weighing approximately 223 g was placed on top of the acquisition layer with the hole centered over the center mark. Using a graduated cylinder, 3 ml of test fluid was added through the hole in the strike plate and using a stopwatch, the time required for the test fluid to be absorbed was recorded as the acquisition time in seconds. The strike plate was removed and the sample allowed to equilibrate for 20-minutes. Then the preweighed resin bond acquisition layer was removed from each sample, weighed, and replaced on the center mark. The weight of liquid retained in the resin bond acquisition layer was recorded.

Then the strike plate was replaced on the center mark and a second 3 ml insult was added as before, the acquisition time recorded, the samples allowed to equilibrate for another 20-minutes and then the liquid retained in the acquisition layer was again weighed and recorded.

Modified Circular Bend:

This test is an indication of the resistance a material has to bending in two dimensions at once and is described in its entirety in U.S. Pat. No. 4,950,264. A 37.5 mm square material sample is placed on top of a flat plate centered over a beveled hole in the plate in a tensile tester fixture and a rod is lowered down onto the sample pushing it into the beveled hole. The amount of force required push the center of the sample down into the hole is recorded as the MCB in grams force.

Caliper:

This is measured using an Emveco Electronic Microgage, Model 200A, set to measure material under a 0.0725 psi load.

Lab results for the various example and control materials are recorded below in table 1.

TABLE 1

| Sample Name | Sample Basis Wt (gsm) | Statistic (n = 3) | 1st 3 ml acquisition time (sec) | 2nd 3 ml acquisition time (sec) | 1st Insult fluid retained in ADL (g) | 2nd insult fluid retained in ADL (g) | MCB (gf) |
|---|---|---|---|---|---|---|---|
| CONTROL 1 | 119 | AVERAGE | 8.5 | 44.8 | 0.96 | 1.76 | 8.4 |
|  |  | s | .7 | 2.9 | .2 | .2 | 1 |
| EXAMPLE 1 | 126 | AVERAGE | 4.6 | 24.8 | 0.10 | 0.96 | 12.7 |

TABLE 1-continued

| Sample Name | Sample Basis Wt (gsm) | Statistic (n = 3) | 1st 3 ml acquisition time (sec) | 2nd 3 ml acquisition time (sec) | 1st Insult fluid retained in ADL (g) | 2nd insult fluid retained in ADL (g) | MCB (gf) |
|---|---|---|---|---|---|---|---|
| | | s | .4 | 1.9 | 0.0 | .05 | 2.3 |
| EXAMPLE 2 | 131 | AVERAGE | 5.0 | 21.0 | 0.09 | 1.04 | 7.2 |
| | | s | .5 | 3.6 | .06 | .09 | 1 |
| CONTROL 2 | 135 | AVERAGE | 9.4 | 40.3 | 0.86 | 1.67 | 11.1 |
| | | s | .4 | 3.7 | .2 | .24 | 3.3 |
| CONTROL 1 + Tissue | 120 + 17 | AVERAGE | 7.6 | 34.7 | 0.87 | 2.03 | * |
| | | s | .8 | 5.7 | .09 | .16 | |
| CONTROL 3 | 188 | AVERAGE | 10.8 | 24.2 | 0.09 | 0.53 | 43.3 |
| | | s | 1.1 | 2.5 | .03 | .3 | 5.8 |

* Comprised of two separate layers so MCB isn't suitable

The drying power of the various absorbent laminates is indicated by the amount of fluid remaining in the acquisition layer material. Those materials with stronger drying power left a smaller amount of the fluid insult remaining in the piece of acquisition layer material placed on top.

Both Example 1 and Example 2 materials had significantly less fluid retained in the acquisition layers than Control 1, Control 2, and Control 1+Tissue.

Control 1 lacks the feature of the highly porous middle layer and the facing layers are less porous.

Control 2 has a middle tissue layer but it is not highly porous and is the same material as the facing layers so the sheet is also lacking the "hollow" feature.

Control 1+Tissue has the highly porous tissue placed underneath the laminate rather than as a center layer.

Control 3 contains less SAP than the laminates, however it has a good ability to dry the acquisition layer, illustrating the shortcomings of the laminates, particularly the prior art controls. The MCB value for Control 3 is much higher than any of the laminates reflecting its subjective stiffness, which is a reason that the laminates are very attractive as storage core materials.

What is claimed is:

1. A disposable absorbent laminate, comprising;
at least three substrate layers, including first, second and third substrate layers each comprising tissue; and
first and second absorbent matrices respectively positioned between adjacent ones of said substrate layers,
each of said absorbent matrices comprising particulate superabsorbent polymeric material and a network of filamentary adhesive,
said filamentary adhesive adhering to and stabilizing said particulate superabsorbent polymeric material, and adhering adjacent ones of said substrate layers to each other to resist delamination of said disposable absorbent laminate, and
wherein said third one of said substrate layers, positioned intermediate of said first and second substrate layers, exhibits a Frazier porosity of at least about 300 feet$^3$/minute/foot$^2$, and differs from a Frazier porosity of at least one of said first and second substrate layers by at least about 70 feet$^3$/minute/foot$^2$, and wherein said first and second substrate layers each exhibit a Frazier porosity of about 150 feet$^3$/minute/foot$^2$ to 250 feet$^3$/minute/foot$^2$.

2. The disposable absorbent laminate in accordance with claim 1, wherein
said first and second substrate layers exhibit the same porosity.

3. The disposable absorbent laminate in accordance with claim 1, wherein
said third substrate layer exhibits a Frazier porosity that differs from a Frazier porosity of at least one of said first and second substrate layers by at least about 130 feet$^3$/minute/foot$^2$.

4. The disposable absorbent laminate in accordance with claim 1, wherein
said disposable absorbent laminate exhibits a modified circular bend value of less than about 30 grams F.

5. The disposable absorbent laminate in accordance with claim 1, wherein
said disposable absorbent laminate exhibits a tensile strength of at least about 10 Newtons per 50 mm (N/50 mm).

6. A disposable absorbent article, comprising:
the disposable absorbent laminate in accordance with claim 1;
a liquid permeable topsheet positioned above said disposable absorbent laminate;
an acquisition/distribution layer positioned between said topsheet and said disposable absorbent laminate; and
a liquid impermeable backsheet positioned beneath said disposable absorbent laminate.

7. The disposable absorbent laminate in accordance with claim 1, wherein said first and second substrate layers each exhibit a basis weight of about 15 to 20 grams/meter$^2$ (gsm), and wherein said third substrate layer exhibits a basis weight of about 15 to 25 gsm.

8. The disposable absorbent laminate in accordance with claim 1, wherein said third substrate layer exhibits a Frazier porosity of at least about 320 feet$^3$/minute/foot$^2$.

9. An absorbent laminate, comprising:
first, second and third substrates each comprising tissue; and
first and second absorbent matrices respectively positioned between said first and third substrates, and said second and third substrates,
each of said absorbent matrices comprising particulate superabsorbent polymeric material and filamentary adhesive, wherein the filamentary adhesive adheres to and stabilizes the particulate superabsorbent material and the two of said substrates adjacent to each absorbent matrix,
said third one of said substrates, positioned intermediate of said first and second absorbent matrices, exhibits porosity which is greater than the porosity of said first and second substrates, and
said third substrate exhibits a Frazier porosity of at least about 300 feet$^3$/minute/foot$^2$, said third substrate exhibiting a Frazier porosity which differs from a Frazier porosity of either one of said first and second substrates by at least about 100 feet$^3$/minute/foot$^2$, and wherein said first and second substrates each exhibit a Frazier porosity of about 150 feet$^3$/minute/foot$^2$ to 250 feet$^3$/minute/foot$^2$.

10. The absorbent laminate in accordance with claim 9, wherein
said second substrate comprises creped tissue.

11. The absorbent laminate in accordance with claim 9, wherein
said absorbent laminate exhibits a modified circular bend value of less than about 30 grams F.

12. The absorbent laminate in accordance with claim 11, wherein
said absorbent laminate exhibits a tensile strength of at least about 10 Newtons per 50 mm (N/50 mm).

13. The absorbent laminate in accordance with claim 9, wherein
said absorbent laminate is symmetrical in a Z-direction.

\* \* \* \* \*